(12) United States Patent
Owman

(10) Patent No.: US 6,333,163 B1
(45) Date of Patent: Dec. 25, 2001

(54) METHOD OF FACILITATING HIV-1 INFECTION THROUGH HUMAN LEUKOTRIENE B4 RECEPTOR

(75) Inventor: Christer Owman, Lund (SE)

(73) Assignee: Owman Invest, Ltd., Lund (SE)

( * ) Notice: Subject to any disclaimer, the term of this patent is extended or adjusted under 35 U.S.C. 154(b) by 0 days.

(21) Appl. No.: 09/365,807

(22) Filed: Aug. 3, 1999

Related U.S. Application Data

(60) Provisional application No. 60/095,450, filed on Aug. 6, 1998.

(51) Int. Cl.$^7$ ................... G01N 33/53; G01N 33/566; G01N 33/569; C12N 15/19; C07K 14/00
(52) U.S. Cl. ................... 435/7.2; 435/325; 435/335; 435/339.1; 435/358; 435/361; 435/363; 435/354; 435/343.1; 530/350
(58) Field of Search ................... 435/7.2, 325, 5, 435/334, 339.1, 358, 361, 363, 354; 530/350

(56) References Cited

PUBLICATIONS

Owman et al. Proc. natl. Acad. Sci. USA , Aug. 4th, 1998, vol. 95, pp. 9530–9534.*

Gifford et al. J. Immunol. Feb. 15, 1987, vol. 138, pp. 1184–1189.*

G. Alkhatib et al., "CC CKR5: A RANTES, MIP–1α, MIP–1β Receptor as a Fusion Cofactor for Macrophage–Tropice HIV–1," *Science*, vol. 272, pp. 1955–1958, Jun. 28, 1996.

H. Deng et al., "Expression cloning of new receptors used by simian and human immunodeficiency viruses," *Nature*, vol. 388, pp. 296–300, Jul. 17, 1997.

T. Dragic et al., "HIV–1 entry into CD4$^+$ cells is mediated by the chemokine receptor CC–CKR–5," *Nature*, vol. 381, pp. 667–673, Jun. 20, 1996.

H. Choe et al., "The β–Chemokine Receptors CCR3 and CCR5 Facilitate Infection by Primary HIV–1 Isolates," *Cell*, vol. 85, pp. 1135–1148, Jun. 28, 1996.

B. Doranz et al., "A Dual–Tropic Primary HIV–1 Isolate That Uses Fusin and the β–Chemokine Receptors CKR–5, CKR–3 and CKR–2b as Fusion Cofactors," *Cell*, vol. 85, pp. 1149–1158, Jun. 28, 1996.

Y. Feng et al., "HIV–1 Entry Cofactor: Functional cDNA Cloning of a Seven–Transmembrane, G Protein–Coupled Receptor," *Science*, vol. 272, pp. 872–877, May 10, 1996.

F. Cocchi et al., "Identification of RANTES, MIP–1α, and MIP–1β as the Major HIV–Suppressive Factors Produced by CD8$^+$ T Cells," *Science*, vol. 270, pp. 1811–1815, Dec 15, 1995.

L. Zhang et al., "HIV–1 subtype and second–receptor use," *Nature*, vol. 383, p. 768, Oct. 31, 1996.

M. Jansson et al., "Sensitivity to inhibition by β–chemokines correlates with biological phenotypes of primary HIV–1 isolates," *Proc. Natl. Acad. Sci. USA*, vol. 93, pp. 15382–15387, Dec. 1996.

G. Simmons et al., "Primary, Syncytium–Inducing Human Immunodeficiency Virus Type 1 Isolates Are Dual–Tropic and Most An Use Either Lestr or CCR5 as Coreceptors for Virus Entry," *J. Virol.*, vol. 70, No. 12, pp. 8355–8360, Dec. 1996.

R. Connor et al., "Change in Coreceptor Use Correlates with Disease Progression in HIV–1–Infected Individuals," *J. Exp. Med.*, vol. 185, No. 4, pp. 621–628, Feb. 17, 1997.

S. Kozak et al., "CD4, CXCR–4, and CCR–5 Dependencies for Infections by Primary Patient and Laboratory–Adapted Isolates of Human Immunodeficiency Virus Type 1," *J. Virol.*, vol. 71, No. 2, pp. 873–882, Feb. 1997.

F. Liao et al., "STRL33, A Novel Chemokine Receptor–like Protein, Functions as a Fusion Cofactor for Both Macrophage–tropic and T Cell Line–tropic HIV–1," *J. Exp. Med.*, vol. 185, No. 11, pp. 2015–2023, Jun. 2, 1997.

H. Deng et al., "Identification of a major co–receptor for primary isolates of HIV–1," *Nature*, vol. 381, p. 661–666, Jun. 20, 1996.

M. Loetscher et al., "TYMSTR, a putative chemokine receptor selectively expressed in activated T cells, exhibits HIV–1, coreceptor function," *Curr. Biol.*, vol. 7, No. 8, pp. 652–660, Aug. 1997.

P. Murphy, "The Molecular Biology of Leukocyte Chemoattractant Receptors[1]," *Ann. Rev. Immunol.*, vol. 12, pp. 593–633, 1994.

C. Owman, et al., "Cloning of cDNA Encoding a Putative Chemoattractant Receptor," *Genomics*, vol. 37, No. 2, pp. 187–194, Oct. 15, 1996.

C. Owman et al., "Leukotriene B$_4$ Is the Functional Ligand Binding to and Activating the Cloned Chemoattractant Receptor," CMKRL1, *Biochem. Biophys. Res. Commun.*, vol. 240, No. 1, pp. 162–166, Nov. 7, 1997.

T. Yokomizo et al., "A G–protein–coupled receptor for leukotriene B$_4$ that mediates chemotaxis," *Nature*, vol. 387, pp. 620–624, Jun. 5, 1997.

N. Landau et al., "Packaging System for Rapid Production of Murine Leukemia Virus Vectors with Variable Tropism," *J. Virol.*, vol. 66, No. 8, pp. 5110–5113, Aug. 1992.

(List continued on next page.)

*Primary Examiner*—James Housel
*Assistant Examiner*—Bao-Qun Li
(74) *Attorney, Agent, or Firm*—Finnegan, Henderson, Farabow, Garrett & Dunner, L.L.P.

(57) ABSTRACT

The present invention provides a human leukotriene B4 receptor that acts as a coreceptor for HIV viruses, polynucleotides encoding the receptor, recombinant cells expressing the receptor, and antibodies against the receptor. The invention also provides methods of identifying drugs that can block viral infection of cells and methods of facilitating infection of cells with HIV viruses.

9 Claims, 4 Drawing Sheets

OTHER PUBLICATIONS

W. Pear et al., "Production of high–titer helper–free retroviruses by transient transfection," *Proc. Natl. Acad. Sci. USA*, vol. 90, No. 18, pp. 8392–8396, Sep. 15, 1993.

J. He et al., "CCR3 and CCR5 are co–receptors for HIV–1 infection of microglia," *Nature*, vol. 385, pp. 645–649, Feb. 13, 1997.

D. Payan et al., "Human T–lymphocyte subset specificity of the regulatory effects of leukotriene $B_4$," *Proc. Natl. Acad. Sci. USA*, vol. 81, No. 11, pp. 3501–3505, Jun. 1984.

M. Rola–Pleszcynski et al., "Identification of Interferon–$\gamma$ As the Lymphokine that Mediates Leukotriene $B_4$–Induced Immunoregulation," *J. Immunol.*, vol. 139, No. 2, pp. 513–517, Jul. 15, 1987.

C. Zachariae et al., "Epidermal lymphocyte chemotatic factor specifically attracts OKT4–positive lymphocytes," *Arch. Dermatol. Res.*, vol. 280, No. 6, pp. 354–357, 1988.

V. Martin et al., "Leukotriene Binding, Signaling, and Analysis of HIV Coreceptor Function in Mouse and Human Leukotriene B4 Receptor–transfected Cells," *J. Biol. Chem.*, vol. 274, No. 13, pp. 8597–8603, Mar. 26, 1999.

* cited by examiner

Transmembrane region III

| | | |
|---|---|---|
| BLTR | - H - - - - V - - Y - S V L - - - - - S L D | (SEQ ID NO. 4) |
| CXCR4 | V H V I Y T V N L Y S S V L I L A F I S L D | (SEQ ID NO. 5) |
| CCR5 | - - - - Y - - - - - S - - - - - - - - - - D | (SEQ ID NO. 6) |

FIG. 4

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:
      SENSE PRIMER FOR AMPLIFYING HIV-1 NUCLEIC ACID.

<400> SEQUENCE: 1
agtagcaacc ctctattgtg tgca                                        24

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence:  ANTISENSE
      PRIMER FOR AMPLIFYING HIV-1 NUCLEIC ACID.

<400> SEQUENCE: 2
acatttgcat ggctgcttga tgt                                         23

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:  PROBE FOR
      DETECTING HIV-1 SEQUENCE.

<400> SEQUENCE: 3
tggctccttc tgataatgct ga                                          22

<210> SEQ ID NO 4
<211> LENGTH: 21
<212> TYPE: PRT
<213> ORGANISM: Homo sapiens
<220> FEATURE:
<221> NAME/KEY: UNSURE
<222> LOCATION: (1)
<223> OTHER INFORMATION: X AT POSITION 1 IS UNDEFINED.
```

```
<221> NAME/KEY: UNSURE
<222> LOCATION: (3)..(6)
<223> OTHER INFORMATION: X AT POSITIONS 3-6 ARE UNDEFINED.
<221> NAME/KEY: UNSURE
<222> LOCATION: (8)..(9)
<223> OTHER INFORMATION: X AT POSITIONS 8 AND 9 ARE UNDEFINED.
<221> NAME/KEY: UNSURE
<222> LOCATION: (11)
<223> OTHER INFORMATION: X AT POSITION 11 IS UNDEFINED.
<221> NAME/KEY: UNSURE
<222> LOCATION: (15)..(18)
<223> OTHER INFORMATION: X AT POSITIONS 15-18 ARE UNDEFINED.

<400> SEQUENCE: 4

Xaa His Xaa Xaa Xaa Xaa Val Xaa Xaa Tyr Xaa Ser Val Leu Xaa Xaa
 1               5                  10                  15

Xaa Xaa Ser Leu Asp
            20

<210> SEQ ID NO 5
<211> LENGTH: 22
<212> TYPE: PRT
<213> ORGANISM: Homo sapiens

<400> SEQUENCE: 5

Val His Val Ile Tyr Thr Val Asn Leu Tyr Ser Ser Val Leu Ile Leu
 1               5                  10                  15

Ala Phe Ile Ser Leu Asp
            20

<210> SEQ ID NO 6
<211> LENGTH: 22
<212> TYPE: PRT
<213> ORGANISM: Homo sapiens
<220> FEATURE:
<221> NAME/KEY: UNSURE
<222> LOCATION: (1)..(4)
<223> OTHER INFORMATION: X AT POSITIONS 1-4 ARE UNDEFINED.
<221> NAME/KEY: UNSURE
<222> LOCATION: (6)..(10)
<223> OTHER INFORMATION: X AT POSITIONS 6-10 ARE UNDEFINED.
<221> NAME/KEY: UNSURE
<222> LOCATION: (12)..(21)
<223> OTHER INFORMATION: X AT POSITIONS 12-21 ARE UNDEFINED.

<400> SEQUENCE: 6

Xaa Xaa Xaa Xaa Tyr Xaa Xaa Xaa Xaa Xaa Ser Xaa Xaa Xaa Xaa Xaa
 1               5                  10                  15

Xaa Xaa Xaa Xaa Xaa Asp
            20
```

METHOD OF FACILITATING HIV-1 INFECTION THROUGH HUMAN LEUKOTRIENE B4 RECEPTOR

CROSS-REFERENCE TO RELATED APPLICATIONS

This application depends on, and claims benefit of, U.S. Provisional Application Ser. No. 60/095,450, filed Aug. 6, 1998 in its entirety by reference.

BACKGROUND OF THE INVENTION

1. Field of the Invention

The present invention relates to a novel chemoattractant receptor and its use. More particularly, this invention relates to a novel heptahelix-type chemokine receptor which naturally binds leukotriene B4 and also serves as a coreceptor facilitating entry of human immunodeficiency virus type 1 (HIV-1) into cells expressing CD4, and methods for using this novel receptor in HIV infectivity and drug screening studies.

2. Description of Related Art

It is now well understood that HIV-1 infection is initiated by interaction of the virion envelope glycoproteins (gpl120/41) with at least two classes of cell membrane receptors. First, the virus associates with the CD4 receptor (1–3), which induces conformational changes in the glycoprotein envelope (4, 5), allowing the virus to subsequently bind to a seven-transmembrane envelope with the cell membrane leading to viral entry. Two major coreceptors have been identified, both belonging to the chemokine family of G-protein coupled receptors.

Macrophage-tropic (M-tropic) strains of HIV, which replicate in macrophages and CD4+T-cells use the β-chemokine receptor CCR5 (6–10). T-tropic isolates of HIV, which replicate in primary CD4+T cells, established CD4+T cell lines, as well as macrophages, use the α-chemokine receptor CXCR4 (11).

A key observation leading to the recent discovery of the viral entry cofactors was the finding that certain β-chemokines have a strong suppressive effect on the HIV-1 infection in vitro (12). Analysis of viral isolates obtained sequentially from infected individuals has shown a loss of sensitivity to inhibition by β-chemokines along with a shift in virus phenotype from a non-syncytium-inducing (NSI) to a syncytium-inducing (SI) phenotype (13–17). This suggests that there is a shift in chemokine receptor usage from CCR5 to CXCR4 as the infection progresses. This is in accordance with the findings that dual-tropic virus strains utilize both types of coreceptors, and that additional coreceptors exist for certain subsets of primary viruses, in addition to their primary usage of CCR5 or CXCR4 (9, 10, 18–20). Hence, the usage of the two major cofactors may be viewed as extremes in an adaption process, along which the virus expands its coreceptor usage to include several different receptors.

Among the superfamily of G-protein coupled, or heptahelix, receptors the chemokine ones form a structurally related group that belongs to the subfamily of leukocyte chemoattractant receptors, which also includes receptors for the so-called classical chemoattractants (24).

Recently, a novel chemoattractant-like receptor, CMKRL1, was cloned (25) whose natural ligand subsequently was shown to be leukotriene B4 (26, 27). This is the first cloned leukotriene receptor, although the leukotrienes themselves, formed from arachidonic acid through the lipooxygenase pathway, have been known for more than two decades (28). The leukotriene B4 receptor, or BLTR, is widely expressed in the immune system (25, 27)—including thymus, spleen, lymph nodes and PBMC—and it shows approximately 30% identity with CCR5 and CXCR4 which, in turn, exhibit the same degree of homology when compared to each other.

Because of the continuing interest in understanding the biology of HIV infection and ways to block such infections, there exists a need in the art for identifying additional HIV coreceptors. In particular, there exists a need in the art for information on the identity, characterization, and efficacy of additional HIV coreceptors. The identification and characterization of additional coreceptors would be particularly advantageous in developing specific therapies for preventing primary HIV infection and limiting the spread of such infections once they have occurred.

Therefore, it is important to search for additional G-protein-coupled receptors that might facilitate the entry of various primary HIV-1 isolates into suitable target cells during the course of the infection. Further, it is important to identify pharmacologically active compounds that inhibit the interaction between the initial HIV-CD4 complex and the coreceptor.

SUMMARY OF THE INVENTION

The present invention provides data showing that CMKRL1 supports the entry of select primary isolates of mainly the SI phenotype into CD4-positive murine host cells. Since, within the group of leukocyte chemoattractant receptors, CMEKRL1/BLTR can be viewed as a "cousin" of the previously identified chemokine-type coreceptors, this hereby introduces an essentially new class of coreceptors that is required for the cellular entry of HIV-1.

Accordingly, this invention aids in fulfilling existing needs in the art. More particularly, this invention provides a B-cell lymphoblast derived heptahelix receptor which naturally binds leukotriene B4 (26, 27) and also acts as a coreceptor for primary isolates of HIV-1. This novel receptor, BLTR, is strongly expressed in lymphoid cells and tissues, including leukocytes, lymph nodes, thymus, spleen, and bone marrow.

Additional features and advantages of the invention will be set forth in the description which follows, and in part will be apparent from the description, or may be learned by practice of the invention. The objectives and other advantages of the invention will be realized and attained by the means of the elements and combinations particularly pointed out in the written description and claims hereof, as well as the appended drawings.

To achieve these and other advantages, and in accordance with the purpose of the invention as embodied and broadly described, the invention comprises a cell line which expresses the human leukotriene B4 receptor on its surface as a result of transfection with DNA sequences encoding BLTR. When CD4 is coexpressed in these cells they are susceptible to infection with certain isolates of HIV-1. Thus, these cells may be useful in characterizing primary HIV infection and coreceptor selection studies.

A cell line capable of surface expression of the human leukotriene B4 receptor may be created by transfecting cells which lack this receptor with DNA fragments or a vector expressing BLTR. The resulting cell line may be stably or transiently transformed, resulting in the expression of human leukotriene B4 receptor.

The present invention also provides recombinant expression vectors comprising the DNA sequences encoding the human leukotriene B4 receptor, recombinant human leukotriene B4 receptor molecules produced using the recombinant expression vectors, and processes for using the expression vectors.

In another embodiment the present invention provides an antibody which specifically binds the human leukotriene B4 receptor and inhibits its ability to function as a viral coreceptor. In addition to blocking membrane fusion, this antibody is useful in a number of diagnostic applications.

In yet another embodiment, the present invention provides a method for screening a drug or other pharmacologically-active agent for its ability to prevent viral infection of cell lines expressing the human leukotriene B4 receptor on its surface.

The accompanying drawings are included to provide a further understanding of the invention and are incorporated in, and constitute a part of, this specification. They are included to illustrate one/several embodiment(s) of the invention and, together with the description, serve to explain the principles of the invention.

BRIEF DESCRIPTION OF THE DRAWINGS

The accompanying drawings, which are incorporated in, and constitute a part of, this specification, illustrate embodiments of the invention and, together with the description, serve to explain the objects, advantages, and principles of the invention.

In the drawings:

FIG. 4 is an alignment of the deduced amino acid sequences for the putative third transmembrane domain of the HIV coreceptors BLTR, CXCR4, and CCR5, showing identical residues of BLTR or CCR5 compared with the full CXCR4 sequence. Non-identical amino acid residues in the BLTR or CCR5 sequences are marked with dashes.

DETAILED DESCRIPTION OF THE PREFERRED EMBODIMENTS

Figure 1:
FIG. 1 shows an autoradiogram from a typical HIV infection experiment using primary virus isolate P001, laboratory HIV isolates IIIb (prototype T-tropic virus), BaL (prototype M-tropic virus), or PCR controls. Lane 1 shows the background level of virus entry into cells expressing CD4 alone. Lanes 2–6 show viral entry into CD4 positive cells coexpressing BLTR (lane 2), CXCR4 (lane 3), CCR5 (lane 4) and positive controls, either CXCR4 cells infected with laboratory virus IIIb (lane 5) or CCR5 cells infected with laboratory virus BaL (lane 6). Lane 7 shows the negative PCR control (K buffer instead of infected cell pellet suspension) and lane 8 shows the positive PQRcontrol (pHXB2 plasmid as PCR template).

The native, mature full-length heptahelix receptor of the invention is a 352 amino acid protein having a deduced molecular weight of 43 kilodaltons, which binds human leukotriene B4 in vivo. This receptor, referred to as BLTR, is widely expressed on immune system cells and shares 30% homology with the chemokine receptors CXCR4 and CCR5.

The BLTR of the invention can be obtained from natural sources or by recombinant techniques using eukaryotic or prokaryotic host systems. "Recombinant" as used herein means that a protein is derived from recombinant (e.g., microbial or mammalian) expression systems. "Microbial" refers to recombinant proteins made in bacterial or fungal (e.g., yeast) expression systems. "Biologically active" as used in this specification as a characteristic of BLTR means that a particular molecule shares sufficient amino acid sequence similarity with embodiments of the present invention to be capable of binding leukotrienes and/or binds to specific HIV isolates when complexed with CD4.

A full-length cDNA, Lyme 21-9, encoding the putative chemoattractant receptor was identified in a human B-cell lymphoblast library by screening with degenerate primers and radiolabeled oligonucleotide probes corresponding to neurotransmitter receptors. Highest expression was found in leukocytes, lymph nodes, thymus and bone marrow (*Cloning of cDNA encoding a putative chemoattractant receptor*, Owman et al., 1996). Subsequent studies demonstrated that the natural ligand of the receptor was the chemokine leukotriene B4 and the receptor was renamed BLTR.

Derivatives of the BLTR heptahelix within the scope of this invention include various structural forms of the primary protein which retain biological activity. Due to the presence of ionizable amino and carboxyl groups, for example, a heptahelix receptor protein can be in the form of acidic or basic salts, or can be in neutral form. Individual amino acid residues can also be modified by oxidation or reduction or replaced by conservative amino acids without significantly decreasing biological activity.

The present invention provides recombinant expression vectors to amplify or express DNA encoding BLTR. Recombinant expression vectors are replicable DNA constructs that have synthetic or cDNA-derived DNA fragments encoding BLTR or bioequivalent analogs operably linked to suitable transcription or translational regulatory elements derived from mammalian, microbial, viral, or insect genes. A transcriptional unit generally comprises an assembly of (1) a genetic element having a regulatory role in gene expression, for example, promoters and/or enhancers; (2) a structural or coding sequence, which is transcribed into mRNA and translated into BLTR or a bioequivalent; (3) appropriate transcription and translation initiation and termination sequences. As will be appreciated by those skilled in the art, modifications and additions to this exemplary transcriptional unit are contemplated by the present invention.

In embodiments, the invention provides an expression vector containing a polynucleotide encoding human leukotriene B4 receptor operably linked to allow expression of the human leukotriene B4 receptor polypeptide.

In accordance with those embodiments directed to an expression vector, the present invention provides a method of facilitating infection of HIV comprising transforming a cell with an expression vector of the invention. The resulting cell will be capable of enhanced rates and levels of infection by HIV virions. In preferred embodiments, the method of facilitating infection of HIV comprises transforming a CD4+ cell with an expression vector of the invention. In addition, the method can comprise transforming a CD4− cell with an expression vector of the invention and a polynucleotide sequence encoding CD4 or a vector containing nucleic acid sequences encoding CD4.

DNA regions are operably linked when they are functionally related to each other. For example, DNA for a signal peptide is operably linked to a polypeptide. DNA if it is expressed as a precursor which participates in the secretion of the polypeptide. A promoter is operably linked to a coding sequence if it controls the transcription of the sequence. A ribosome binding site is operably linked to a coding sequence if it is positioned so as to permit translation. Generally, operably linked means contiguous and, in the case of secretory leader sequences, contiguous and in reading frame.

Structural elements intended for use in yeast expression systems preferably include a leader sequence enabling extracellular secretion of translated protein by a host cell. Alternatively, where recombinant protein is expressed without a leader or transport sequence, it can include an N-terminal methionine residue. This residue can optionally be substantially cleaved from the expressed recombinant protein to provide a final product.

DNA sequences encoding mammalian heptahelix receptors which are to be expressed in a microorganism, preferably contain no introns that could prematurely terminate transcription of DNA into mRNA; however, premature termination of transcription may be desirable, for example, where it would result in mutants having advantageous C-terminal truncations. Due to code degeneracy, there can be considerable variation in nucleotide sequences encoding the same amino acid sequence. Other embodiments include sequences capable of hybridizing to the sequences of the provided cDNA under moderately stringent conditions and other sequences hybridizing or degenerate to those that encode biologically active heptahelix receptor polypeptides.

Recombinant heptahelix receptor DNA can be expressed or amplified in a recombinant expression system comprising a substantially homogenous, monoculture of suitable host microorganisms, for example, bacteria such as *E. coli*, or yeast such as *S. cerevisiae*, which have stably integrated (by transduction or transfection) a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

Transformed host cells are cells that have been transduced or transfected with heptahelix receptor vectors constructed using recombinant DNA techniques. Transformed host cells ordinarily express heptahelix receptor, but host cells transformed for purposes of cloning or amplifying heptahelix receptor DNA do not need to express heptahelix receptor. Expressed heptahelix receptor will be deposited in the cell membrane or secreted into the culture supernatant, depending on the heptahelix receptor DNA selected. Suitable host cells for expression of heptahelix receptor include prokaryotes, yeast, or higher eukaryotic cells under the control of appropriate promoters. Prokaryotes include gram-negative or gram-positive organisms, for example, *E. coli* or other bacilli. Higher eukaryotic cells include established cell lines of mammalian origin. Cell-free translation systems can also be employed to produce heptahelix receptor using RNAs derived from the DNA constructs of the present invention. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), the relevant disclosure of which is hereby incorporated by reference.

Promoters commonly used in recombinant microbial expression vectors include the β-lactamase (penicillinase) and lactose promoter system (Chang et al., *Nature*, 275:615 (1978); and Goeddel et al., *Nucl. Acids Res.*, 8:40575 (1980); and EPA 36,776) and tac promoter (Maniatis, *Molecular Cloning: A Laboratory Manual*, Cold Spring Harbor Laboratory, p. 412 (1982)).

Recombinant heptahelix receptor proteins can also be expressed in yeast hosts, preferably from the Saccharomyces species, such as *S. cerevisiae*. Yeast of other genera, such as Pichia or Kluyveromyces, can also be employed. Yeast vectors will generally contain an origin of replication from the 2μ yeast plasmid or an autonomously replicating sequence (ARS), promoter, DNA encoding heptahelix receptor, sequences for polyadenylation, transcription, and termination, and a selection gene.

Suitable promoter sequences in yeast vectors include the promoters for metallothionein, 3-phosphoglycerate kinase (Hitzeman et al., *J. Biol. Chem.*, 255:2073 (1980)), or other glycolytic enzymes (Hess et al., *J. Adv. Enzyme Reg.*, 7:149 (1968)); and Holland et al., *Biochem.*, 17:4900 (1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, phosphoglucoase isomerase, and glucokinase.

Various mammalian or insect cell culture systems are also advantageously employed to express recombinant protein. Expression of recombinant proteins in mammalian cells is particularly preferred because such proteins are generally correctly folded, appropriately modified, and completely functional. Examples of suitable mammalian host cell lines include the COS-7 lines of monkey kidney cells, described by Gluzman (*Cell*, 23:175 (1981)), and other cell lines capable of expressing an appropriate vector including, for example, L cells, C127, 3T3, Chinese hamster ovary (CHO), HeLa, and BHK cell lines. Mammalian expression vectors can comprise nontranscribed elements, such as an origin of replication, a suitable promoter, and an enhancer linked to the gene to be expressed, and other 5' or 3' nontranslated sequences, such as ribosome binding sites and transcriptional terminal sequences. Baculovirus systems for production of heterologous proteins in insect cells are reviewed by Luckow et al., *BiolTechnology*, 6:47 (1988).

The transcriptional and translational control sequences in expression vectors to be used in transforming vertebrate cells can be provided by viral sources. For example, commonly used promoters and enhancers are derived from polyoma, adenovirus 2, Simian virus 40 (SV40), and human cytomegalovirus. DNA sequences derived from the SV40 viral genome, for example, SV40 origin, early and late promoter, enhancer, splice, and polyadenylation sites, can be used to provide the other genetic elements required for expression of a heterologous DNA sequence.

Purified mammalian heptahelix receptors or analogs can be prepared by culturing suitable host/vector systems to express the recombinant translation products of the DNAs of the present invention, which are then purified from culture media or cell extracts. For example, supernatants from systems that secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise a heptahelix or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose, or other types commonly employed in protein purification.

Finally, one or more reverse-phase high performance liquid chromatography (RP-HPLC) steps employing hydrophobic RP-HPLC media, e.g., silica gel having pendant methyl or other aliphatic groups, can be employed to further purify a heptahelix receptor-containing composition. Some or all of the foregoing purification steps, in various combinations, can also be employed to provide a homogeneous heptahelix receptor.

Recombinant heptahelix receptor produced in bacterial culture can be isolated by initial extraction from cell pellets, followed by one or more concentration, salting-out, aqueous ion exchange, or size exclusion chromatography steps. Finally, high performance liquid chromatography (HPLC) can be employed for final purification steps. Microbial cells employed in expression of recombinant the receptor can be disrupted by any convenient method, including freeze-thaw cycling, sonication, mechanical disruption, or use of cell lysing agents.

In another embodiment, the present invention provides an antibody which specifically binds the human leukotriene B4 receptor and inhibits its ability to function as a viral coreceptor.

In addition to blocking membrane fusion, this antibody is useful in a number of diagnostic applications. Antibodies of the invention can be polyclonal or monoclonal. Preparation of an antibody according to the invention can be carried out using standard techniques known to those of skill in the art. The antibody is preferably an antibody which specifically binds to human leukotriene B4 receptor polypeptide, or fragments thereof. Such an antibody can, for example, block membrane fusion between HIV and a susceptible cell and/or block binding of leukotriene B4 to a receptor.

In yet another embodiment, the present invention provides a method for screening a drug or other pharmacologically-active agent for its ability to prevent viral infection of cell lines expressing the human leukotriene B4 receptor on its surface. In preferred embodiments, the method is used to screen for molecules capable of preventing HIV infection. The method can be a method for screening a drug or other pharmacologically-active agent for its ability to block viral infection of a cell line coexpressing human leukotriene B4 receptor and CD4 on its cell surface, and can comprise the following steps:

(a) propagating the cell line in vitro or in vivo;

(b) exposing the cell line to a primary virus isolate under conditions appropriate for interaction of the primary virus isolate with cell surface-expressed receptors;

(c) removing or diluting the virus to a predetermined detection threshold;

(d) incubating the virus exposed cells for a time sufficient for viral replication to occur; and (e) assaying for virus replication or viral gene expression.

The method can include an assay technique that comprises visual observation of the cells for viral-induced cytopathic effects. It can also include an assay technique that comprises harvesting culture material, exposing susceptible animals or cell lines to the harvested culture material, and quantitating infectivity. Additionally and/or alternatively, the assay technique can comprise measuring levels of antibody binding, hybridizing nucleic acid sequences, or measuring levels of viral protein expression.

EXAMPLES

The invention will be further clarified by the following examples, which are intended to be purely exemplary of the invention.

Example 1

Cells, Viruses, and Techniques
Receptor-Expressing Cells.

NIH3T3 cells (murine fibroblasts) were used to transfect the cDNA encoding various human receptors for stable expression, followed by infection with the different virus isolates.

The experiments focused on the human leukotriene receptor CMKRL1, clone Lyme21-9(25), stably transfected into NIH3T3 CD4 cells. Cells expressing CD4 alone or in combination with CCR5 or CXCR4 (kindly provided by Dr. Dan Littman, Skirball Institute for BioMolecular Medicine, New York Medical Center) were established as previously described (29, 30).

Virus Isolates.

The primary virus isolates were recovered by co-cultivation of PHA (Murex Diagnostics)-activated PBMC or CD8-depleted PBMC from HIV-infected individuals, with PHA-stimulated PBMC from two blood donors. PBMC were separated by Ficoll (Pharmacia Biotech) gradient centrifugation. To improve the efficiency of HIV replication, CD8-positive cells were depleted from the patient's PBMC by immunomagnetic beads (DynaBeads M-450 CD8) according to the manufacturer's (Dynal, Inc.) protocol. Freshly isolated PBMC or CD8-depleted PBMC ($2\times10^6$ cells) were activated with PHA (1 $\mu$g/ml) for 3 days and co-cultivated with PHA blasts from the two normal donors at 1:3 ratio. The cultures were maintained in complete RPMI 1640 medium (BioWhittaker) supplemented with 10% fetal calf serum (Gemini Bio-Products) and 10 ng/ml recombinant human IL-2 (R&D Systems). For a total of 4 weeks the cultures were evaluated for the presence of HIV-1 p24 core antigen by a commercially available ELISA assay (DuPont/NEN). At the time of positive virus cultures, stocks were generated by expanding the isolates in PHA-stimulated donor PBMC, after which the viruses were sterile-filtered, aliquotted, and cryopreserved at $-150°$ C. Following the infection experiments, virus phenotype was determined using the MT-2 cell assay (31). Briefly, MT-2 cells and PHA-activated PBMC from healthy donors were infected with the primary isolates in parallel (16–200 ng per $0.5\times10^6$ cells). MT-2 cell cultures were monitored microscopically for syncytium formation and p24 antigen production. Isolates producing syncytia and p24 antigen in the culture were classified as MT-2 positive with SI phenotype, whereas virus classified as MT-2 negative with NSI phenotype replicated in PBMC but did not induce syncytia or p24 production in MT-2 cells. The clinical isolates are listed in Table 1 along with the patient's blood counts of CD4-positive lymphocytes, the virus phenotype, and p24 levels in the original stock. In control experiments, the prototypic M-tropic isolate, BaL (32), or the T-tropic isolate, IIIb (33), propagated extensively in the neoplastic T-cell line, H9 were used.

TABLE 1

Primary and laboratory isolates of HIV-1 used in the infection experiments: patients and characteristics of the isolates.

| Patient | CD4 count* | Virus isolate | Virus phenotype° | p24 core antigen□ |
|---------|-----------|---------------|-----------------|-------------------|
| A | 400 | DS pbmc CD8⁻ | SI | 150 |
| B | 354 | LR pbmc CD8⁻ | SI | 262 |
| C | 79 | 5774 PBMC | SI | 68 |
| D | — | G3 | NSI | 120 |
| E | 923 | AT pbmc CD8⁻ | SI | 110 |
| F | 411 | P001 pbmc CD8⁻ | SI | 24 |
| G | 386 | L002 PBMC | SI | 336 |
| H | — | 22069-05 | SI | 312 |
| J | — | JV 1083 | NSI | 16 |
| K | — | 571 | SI | 170 |
| — | — | IIIb | SI | 237 |
| — | — | BaL | NSI | 688 |

Primary virus isolates from 10 patients, as well as two laboratory-adapted model isolates, tested on CD4-positive mouse fibroblasts (NIH3T3) expressing various types of human chemotactic receptors.
Primary isolates were grown by coculturing with stimulated human PBMC (in the four isolates designated "pbmc CD8- ", PBMC were depleted of CD8-positive cells using DynaBeads).
G3 and JV1083 are primary isolates from Nigerian clade G/A.
HIV-1 BaL was passaged several times exclusively in primary adherent macrophage cultures derived from peripheral blood. HIV-1 IIIb is a long term laboratory-passaged isolate grown in H9 cells.
*Absolute counts of CD4-positive lymphocytes (cells/mm3) in patients were measured at the time of initial blood draw.
°Phenotype was classified in MT-2 assays following the infection.
□Viral titers were evaluated in vitro using p24 core antigen ELISA assays (ng/ml).

Infection Experiments.

NIH3T3 cells expressing CD4 alone, or in combination with one of the test receptors, were initially grown for at least two passages before $10^5$ or $2 \times 10^5$ cells were seeded in 6-well plates. On the following day they were infected with the various primary isolates (10–75 ng of p24 antigen) or the laboratory isolates, BaL or IIIb (10 ng of p24 antigen), for 2 h at 37° C. The cells were then washed three times with PBS and resuspended in complete culture medium DMEM containing 10% bovine serum) and grown for another 16 h. They were harvested, washed several times in cell medium, and pelleted by centrifugation. The supernatant was removed and the pellet stored until further analysis at -20° C. PCR Amplification of HIV-1 DNA.

The infected cell pellet was dissolved at room temperature (approximately 21–25° C.) in 100 µl K buffer containing 100 µg/ml of proteinase K, followed by incubation at 55° C. for 60 min, after which the protease was inactivated at 95° C. for 10 min (34). Ten µl of the suspension was used as template in 50-µl PCR reactions for semiquantitative amplification of the gag region of HIV-1 using recombinant Taq DNA polymerase (Gibco BRL) in 35 cycles, each consisting of 94° C. 45 sec denaturing (pseudo-hot start), 550° C. 1 min annealing, 72° C. 1 min extension, and 72° C. 7 min final extension. After every sixteenth PCR sample a negative control was included (K buffer instead of pellet suspension as template) followed by a positive control (10 ng of pHXB2, a full-length proviral clone derived from the IIIb isolate (35, 36). The sense primer, SK 38 (5'-AGTAGCAACCCTCTATTGTGTGCA-3') (SEQ ID NO:1), corresponded to nucleotides, 1030–1053 of the pHXB2 sequence, and the antisense primer, SK 39 (5'-ACATTTGCATGGCTGCTTGATGT-3') (SEQ ID NO:2), corresponded to nucleotides 1367–1389. The 360-bp PCR product was separated by 1.5% agarose gel electrophoresis (10 µl per lane), transferred to a nitrocellulose membrane filter, and hybridized with a $^{32}$P-labelled internal probe (5'-TGGCTCCTTCTGATAATGCTGA-3') (SEQ ID NO:3), which corresponds to nucleotides 1305–1326 in the pHXB2 sequence. The filters were exposed to Kodak X-Omat AR film for 24 h.

Computer-assisted Densitometry.

The intensity of the hybridization signals from the bands in the autoradiograms was measured using NIH Image software version 1.61 following image acquisition with a CCD camera. The optical densities of the individual bands were recorded, and the film background as well as the respective biological background (electrophoretic bands obtained following infection of cells expressing CD4 alone) were then subtracted. Comparison was made only between values obtained in the same set of experiments, based on simultaneous PCR-amplifications and lined up in the same autoradiogram. Results from repeated experiments were averaged together.

Example 2

Infection of Host Cells

Figure 2:
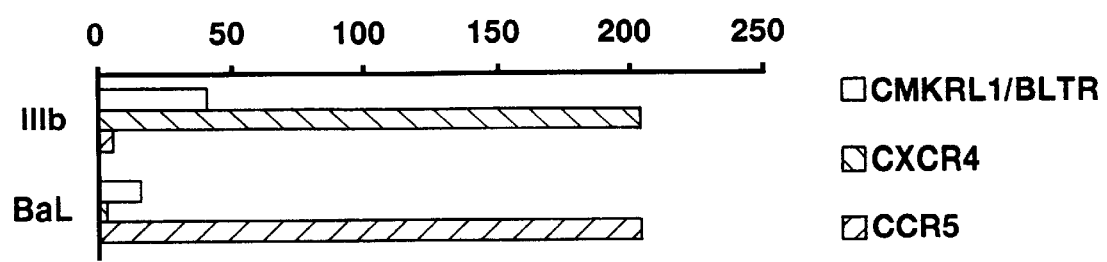
FIG. 2 depicts, in graphical form, infection of CD4-positive NIH3T3 cells (murine fibroblasts) coexpressing three different human chemotactic receptors (CMKRL1/BLTR, CXCR4, and CCR5), with the two laboratory-adapted model isolates, IIIb and BaL (see Table 1). The graph illustrates computer-assisted densitometry of the autoradiograms and is expressed as relative density (number of pixels) of the hybridizing bands following subtraction of the film background and any positive signal from control cells expressing CD4 alone. After 16 h exposure to the various isolates, viral cDNA was amplified in semiquantitative PCR reactions followed by hybridization of southern blots with a $^{32}$P-labelled, 22-mer oligonucleotide probe internal to the pHXB2 viral sequence. Bars show averages from 2–4 experiments, the standard deviation being less than 20% of the mean absolute pixel values.

Entry of HIV-1 into the murine host cell model was estimated in terms of the amount of PCR-amplified virus DNA measured by computer-assisted densitometry in Southern blots following cellular uptake and reverse transcription of viral RNA (FIG. 1). In order to adjust the infectious dose so that little or no virus entry (corresponding to a mean optical density that yielded pixel values between 0 and 15, on a scale of 0 to 255) occurred in NIH3T3.CD4 control cells, pilot titration experiments were performed using BaL at 1, 5, 10, 15 and 20 ng of p24 antigen. The optimal dose was found to be 10 ng. In all experiments testing primary isolates, this dose of IIIb or BaL was used as a positive control following infection of NIH3T3.CD4 cells coexpressing their respective model receptor, CXCR4 or CCR5 (FIG. 1). As shown in FIG. 2, coexpression of either of these coreceptors increased the entry of the corresponding virus strain into the cells to a mean optical density of 200 pixels. The graph also shows that the "cross-entry" of BaL into cells expressing CXCR4, or IIIb in the presence of CCR5, was insignificant.

Figure 3:
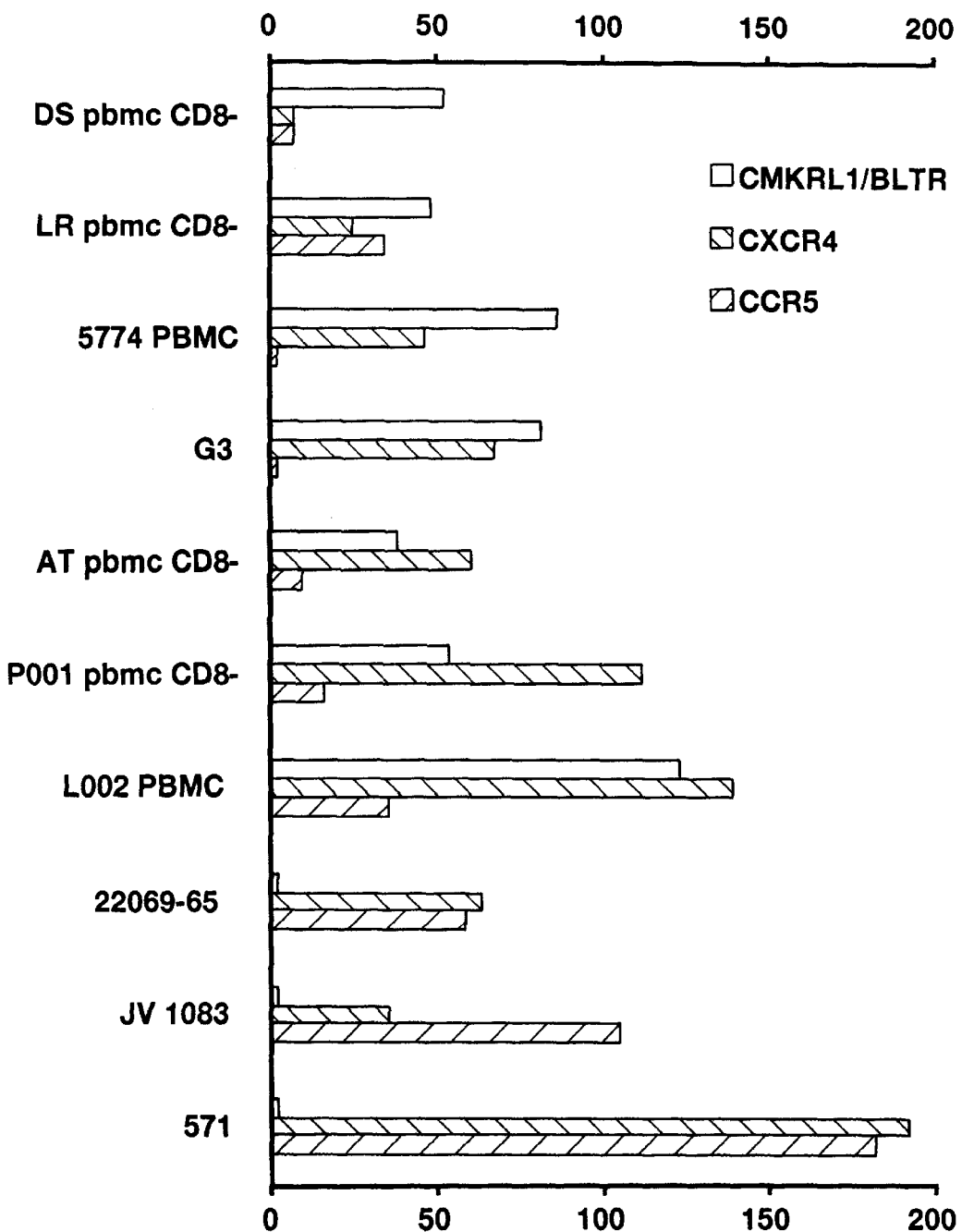
FIG. 3 depicts, in graphical form, results of infection experiments of CD4-positive NIH3T3 cells (murine fibroblasts), coexpressing three different human chemotactic receptors (CMKRL1/BLTR, CXCR4, and CCR5), with 10 clinical isolates of HIV-1 presented in Table 1. The infection experiments were performed as in FIG. 2.

Pilot experiments were also carried out with the primary isolates in order to adjust the dose levels to a negligible non-specific entry of virus into the CD4-positive control cells (FIG. 1), and subsequent experiments were carried out at the 40 ng dose. There was approximately a 50-fold increase in the cellular entry of patient isolates A-G when testing cells expressing CMKRL1 compared to the CD4-positive controls (FIG. 3). All isolates (except DS pbmc CD8-) also entered cells which instead expressed CXCR4. In the case of isolates A-D, the entry into cells expressing CMKRL1 was even higher than the entry into cells equipped with CXCR4. A particular high level of viral entry into cells expressing CMKRLI was observed when the titer of the isolate L002 had been increased by passaging in PBMC (FIG. 3).

In accordance with the mainly SI characteristics of isolates A–G, the usage of CCR5 was in most instances (except for isolate LR pbmc CD8-) lower than that of CXCR4 (FIG. 3). This is in contrast to the situation with isolates H-K, which entered to a high degree both into CD4-positive cells expressing CXCR4 and into those equipped with CCR5. None of these isolates utilized CMKRL1 for their entry (FIG. 3). When comparing FIGS. 2 and 3 it is evident that in most instances the primary virus isolates utilized the major coreceptors, CXCR4 and CCR5, less efficiently than the laboratory-adapted isolates utilized the same coreceptors.

Consistent with the above findings on the clinical isolates also the SI-type of laboratory isolate, IIIb, showed a significant entry into cells expressing CMKRL1 (FIG. 2), in addition to the (very high) entry into cells transfected with CXCR4. BaL, on the other hand, which was efficiently taken up into CD4-positive cells equipped with CCR5, did not enter CMKRL1-expressing cells to any significant degree (FIG. 2).

This example utilizes a cell model in which various human chemotactic receptors are stably expressed together with human CD4 in otherwise non-permissive mouse fibroblasts. Infection experiments were carried out with 10 primary isolates of HIV-1, followed by semiquantitative PCR amplification of viral cDNA. They suggest that a new type of chemotactic membrane receptor—the leukotriene B4 receptor, BLTR—is required for the entry of certain, primarily SI-type, clinical isolates into CD4-positive target cells. In accordance with their SI phenotype, the isolates also efficiently utilize the major chemokine receptor, CXCR4, but not CCR5.

Several types of target cells have been utilized in previous infection experiments, among them NIH3T3 mouse fibroblasts (7, 8, 11), which were found to be favorable because they are basically non-permissive due to the lack of necessary (human) membrane receptors. Moreover, murine cells transfected with human CD4 are resistant to infection with all tested strains of HIV-1 (7). Accordingly, any entry of test isolates into such cells could be minimize when non-specific uptake of virus particles was eliminated by properly reducing infectious dose or exposure time in the infection assays. It could also be confirmed that coexpression (together with CD4) of human CXCR4 (11) or CCR5 (7) led to a prominent entry of prototypic isolates of T- or M-tropic virus strains, respectively. These reactions were therefore used as positive biological controls along with the clinical test isolates.

The PCR-based amplification of viral cDNA provides a useful means to evaluate cellular entry and intracellular reverse transcription of HIV-1 (21). In calibration trials with the pHXB2, a full-length clone derived from HIV-1 IIIb (35, 36), which was used throughout this example as an internal control for the PCR reactions, the method has been found to yield a semiquantitative reflection of the number of viral DNA copies present during the course of the infection in vitro (21). Therefore, the degree of infection with the clinical isolates was chosen as the level of increase of viral cDNA in cells stably expressing the various test receptors, beyond the level in control cells expressing CD4 alone.

The presently identified new HIV coreceptor was originally cloned as an "orphan" G-protein linked, heptahelix receptor showing structural similarities to receptors in the chemoattractant family and provisionally named CMKRL1 (25). At the time when the molecular genetic features of this receptor was submitted for publication, the two chemoattractant receptors, CXCR4 (then an "orphan" receptor, too) and CCR5, had just been identified as HIV coreceptors (6–11). It was striking that all three receptors showed some 30% overall sequence similarity. Moreover, the distribution of CMKRL 1 in cells and tissues of the immune system (25) would make this new receptor a suitable target for HIV-1. With this in mind we set out to investigate whether also CMKRL1 could function as an entry cofactor for HIV-1. This was timely stimulated by observations indicating that further coreceptors seemed to exist which, in concert with either of the two major coreceptors, could facilitate cellular entry of various HIV strains (9, 10).

In the course of developing this invention, leukotriene B4 was, in separate studies (26, 27), identified as ligand for CMKRL1 which is, thus, the first cloned member the leukotriene receptor family. Among hitherto identified HIV coreceptors, the characteristics of CCR5 and CXCR4 are well understood in terms of their interaction with M- and T-tropic virus strains (6–11). Dual-tropic isolates utilize both receptors (10). CCR2b seems to be restricted to its support of one specific dual-tropic isolate (10), whereas CCR3 facilitates infection with certain of the M-tropic isolates that also utilize CCR5 (9, 10, 37). A couple of additional β-chemokine receptors have more recently been shown to support HIV-1 entry of not only M-tropic (19) but also T-tropic (18) virus strains. It seems to be a general feature that the "assisting" coreceptors are less, or sometimes much less, efficient in supporting virus infection than the major coreceptor, CCR5. Besides CXCR4, there does not seem to be any further HIV coreceptor of the α-chemokine type known to date.

The present example introduces the recently cloned leukotriene B4 receptor, CMKRL1/BLTR (25–27), as a new type of "assisting" of HIV-1 coreceptor for select primary viruses. Clinical isolates were used because they should more closely reflect the actual mode of viral usage at a given disease stage than isolates which have been passaged and adapted in immortalized cell lines. The murine target cell model used reflects a limited, albeit crucial, phase in the virus life span, namely the cellular entry and subsequent retrograde transcription. Preliminary data using an entirely different infection model of human astrocytes coexpressing CD4 and CMKRL1 has been obtained, and indicates that the receptor supports the infection also of yet another SI-type isolate (designated LW), as reflected in p24 ELISA measurements. The pathophysiological significance of the new coreceptor, CMKRL1/BLTR, is emphasized by the fact that, like previously identified coreceptors, it is widely distributed in the human immune system (25, 27) where it is expressed also in CD4-positive cells (38–40). The new receptor differs in that the major coreceptor "partner" is CXCR4 rather than CCR5. This agrees with the finding that the virus isolates utilizing CMKRL1/BLTR turned out to be of the SI phenotype (except the G3 isolate, which is of a different genotype and in an uncharacteristic manner utilized CXCR4, although it was classified as NSI phenotype). Also the laboratory-adapted, T-tropic protoype virus strain, IIIb, was taken up into the test cells expressing CMKRL1/BLTR, but only with some 25% of the uptake efficiency provided by its model corecepor, CXCR4. The three isolates that did not utilize CMKRL1/BLTR all behaved like "dual-tropic" types of isolates (10).

There is direct experimental evidence that the interaction between gp120 and CD4 induces conformational changes, which promote the physical association of the complex with the coreceptor (41–43). The search for determinants of HIV entry by way of the chemokine receptors has revealed a complex picture. All of the extracellular domains of these receptors seem to play a role in viral entry, although the amino-terminus and the second extracellular domain seem to be particularly important in this regard (44–48). The fuision activity of the receptor does not require G-protein signalling (49). Since the isolates utilizing BLTR as coreceptor also entered cells expres sing CXCR4 (rather than CCR5) it should be important to elucidate any structural similarities between the first two receptors. Thus, Thr-3 and Phe-16 in BLTR (25, 27) correspond to identical residues in CXCR4, whereas Ser and Ile are found in the respective positions of CCR5. Another region of the receptor that stands out is the third transmembrane helix domain (FIG. 4), where eight distinct residues (including such a functionally important residue as His) are identical between BLTR and CXCR4; only two are identical between the latter and CCR5. In all other transmembrane or extracellular domains, at the most, four residues are identical between the first two receptors, whereas in those regions the identities between CXCR4 and CCR5 are always more numerous. Although most of the modelling aimed at elucidating virus-coreceptor interaction has focused on the extracellular domains of the receptor (44–48), proper knowledge about the three-dimensional configuration of the receptor molecule is still lacking which hampers the detailed mapping of virus-binding epitopes. Thus, paradoxical results have been obtained with chimeric receptor constructs, and much of these results indicate that trans-membrane and cytoplasmic domains may also make major contributions to coreceptor function (47).

The novel type of HIV-1 coreceptor of the present invention, and the data presented herein, emphasize that a whole array of membrane receptors may be utilized by the virus when it adapts over a long period of time. Such receptors may not be found only within a single family (of chemokines) but may involve also other, structurally related but distinct, receptors outside the family. The decisive criterion might be in which cell type, or how extensive among various types of cells, the coreceptor is expressed in order to serve as a suitable vehicle for the virus when it invades the cell.

REFERENCES

1. Dalgleish, A. G., Beverly, P. C. L., Clapham, P. R., Crawford, D. H., Greaves, M. F. & Weiss, R. A. (1984) *Nature* 312, 763–767.
2. Klatzmann, D., Champagne, E., Chamaret, S., Gruest, J., Guetard, D., Hercend, T., Gluckman, J. C. & Montagnier, L. (1984) *Nature* 312, 767–768.
3. Maddon, P., Dalgleish, A., McDougal, J. S., Clapham, P., Weiss, R., & Axel, R. (1986) *Cell* 47, 333–348.
4. Sattenau, Q. J., Zolla-Pazner, S. & Poignard, P. (1995) *Virology* 206, 713–714.
5. Chan, D. C., Fass, D., Berger, J. M. & Kim, P. S. (1997) *Cell* 89, 263–273.
6. Alkhatib, G., Combadiere, C., Broder, C. C., Feng, Y., Kennedy, P. E., Murphy, P. M. & Berger, E. A. (1996) *Science* 272, 1955–1958.
7. Deng, H.-K, Liu, R., Ellmeier, W., Choe, S., Unutmaz, D., Burkhart, M., Di Marzio, P., Marmon, S., Sutton, R. E., Hill, C. M., Davis, C. B., Peiper, S. C., Schall, T. J., Littman, D. R., & Landau, N. R. (1996) *Nature* 381, 661–666.
8. Dragic, T., Litwin, V., Allaway, G. P., Martin, S. R., Huang, X., Nagashima, K. A., Cayanan, C., Maddon, P. J., Koup, R. A., Moore, J. P. & Paxton, W. A. (1996) *Nature* 381, 667–673.
9. Choe, H., Farzan, M., Sun, Y., Sullivan, N., Rollins, B., Ponath, P. D., Wu, L., Mackay, C. R., LaRosa, G., Newman, W., Gerard, N., Gerard, C., & Sodorski, J. (1996) *Cell* 85, 1135–1148.
10. Doranz, B., J., Rucker, J., Yi, Y., Smyth, R. J., Samson, M., Peiper, S. C., Parmentier, M., Collman, R. G., & Doms, R. W. (1996) *Cell* 85, 1149–1158.
11. Feng, Y., Broder, C. C., Kennedy, P. E., & Berger, E. A. (1996) *Science* 272, 872–877.
12. Cocchi, F., DeVico, A. L., Garzino-Demo, A., Arya, S. K., Gallo, R. C., & Lusso, P. (1995) *Science* 270, 1811–1815.
13. Zhang, L., Huang, Y., He, T., Cao, Y. & Ho, D. D. (1996) *Nature* 383, 768, 1996.
14. Jansson, M., Popovic, M., Karlsson, A., Cocchi, F., Rossi, P., Albert, J., & Wigzell, H. (1996) *Proc. Natl. Acad. Sci. USA* 93, 15382–15387.
15. Simmons, G., Wilkinson, D., Reeves, J. D., Dittmar, M. T., Beddows, S., Weber, J., Carnegie, G., Desselberger, U., Gray, P. W., Weiss, R. A. & Clapham, P. R. (1996) *J. Virol.* 70, 8355–8360.
16. Connor, R. I., Sheridan, K. E., Ceradini, D., Choe, S. & Landau, N. R. (1997) *J. Exp. Med.* 185, 621–628.
17. Kozak, S. L., Platt, E. J., Madani, N., Ferro, F. J., Feden, K. & Kabat, D. (1997) *J. Virol.* 71, 873–882.
18. Liao, F., Alkhatib, G., Peden, K. W. C., Sharma, G., Berger, E. A., & Farber, J. M. (1997) *J. Exp. Med.* 185,2015–2023.
19. Deng, H.-K., Unutmaz, D., Kewal Ramani, V. N., & Littman, D. R. (1997) *Nature* 388, 296–300.
20. Loetscher, M., Amara, A., Oberlin, E., Brass, N., Legler, D. F., Loetscher, P., D'Apuzzo, M., Meese, E., Rousset, D., Virelizier, J.-L., Baggiolini, M., Arenzana-Seisdedos, F., & Moser, B. (1997) *Curr. Biol.* 7, 652–660.
21. Cocchi, F., DeVico, A. L., Garzino-Demo, A., Cara, A., Gallo, R.C. & Lusso, P. (1996) *Nature Med.* 2, 1244–1247.
22. Oravecz, P., Pall, M. & Norcross, M. A. (1996) *J. Immunol.* 157, 1329–1332.
23. Speck, R. F., Wehrly, K., Platt, E. J., Atchison, R. E., Charo, I. F., Kabat, D., Chesebro, B. & Goldsmith, M. A. (1997) *J. Virol.* 71, 7136–7139.
24. Murphy, P. M. (1994) *Ann. Rev. Immunol.* 12, 593–633.
25. Owman, C., Nilsson, C., & Lolait, S. J. (1996) *Genomics* 37, 187–194.
26. Owman, C., Sabirsh, A., Boketofi, A. & Olde, B. (1997) *Biochem. Biophys. Res. Commun.* 240, 162–166.
27. Yokomizu, T., Izumi, T., Chang, K., Tukawa, Y. & Shimizu, T. (1997) *Nature* 387, 620–624.
28. Samuelsson, B. (1980) *TiPS* 1, 227–230.
29. Landau, N. R. & Littman, D. R. (1992) *J. Virol.* 66, 5110–5113.
30. Pear, W. S., Nolan, G. P., Scott, M. L. & Baltimore, D. (19993) *Proc. Natl. Acad. Sci. USA* 90, 8392–8396.
31. Karlsson, A., Parsmyr, K., Sandstrom, E., Fenyo, E. M. & Albert, J. (1994)*J. Clin. Microbiol.* 32, 364–370.
32. Gartner, S., Markovits, P., Markovits, D. M., Kaplan, M. H., Gallo, R. C. & Popovic, M. (1986) *Science* 233, 215–219.
33. Popovic, M., Samgadharan, M. G., Read, E. & Gallo, R. C. (1984) *Science* 224, 497–500.
34. Kawasaki, E. S. (1990) in *PCR Protocols: A Guide to Methods and Applications*, eds Innis, M. A., Gelfand, D. H., Sninsky, J. J. & White, T. J. (Academic Press, New York), pp. 146–152.
35. Fisher, A. G., Collalti, E., Ratner, L., Gallo, R. C. & Wong-Staal, F. (1985) *Nature* 316, 262–265.
36. Feinberg, M. B., Jarrett, R. F., Aldovini, A., Gallo, R. C. & Wong-Staal, F. (1986) *Cell* 46, 807–817.
37. He, J., Chen, Y., Farzan, M., Choe, H., Ohagen, A., Gartner, S., Busciglio, J., Yang, X., Hofmann, W., Newman, W., Mackay, C. R., Sodorski, J. & Gabuzda, D. (1997) *Nature* 385, 645–649.
38. Payan, D. G., Missirian-Bastian, A. & Goetzl, E. J. (1984) *Proc. Natl. Acad. Sci. USA* 81, 3501–3505.
39. Rola-Pleszczynski, M., Bouvrette, L., Gingras, D. & Girard, M. (1987) *J. Immunol.* 139, 513–517.

40. Zachariae, C., Temowitz, T., Larsen, C. G., Nielsen, V. & Thestrup-Pedersen, K. (1988) *Arch. Dermatol. Res.* 280, 354–357.
41. Wu, L., Gerard, N. P., Wyatt, R., Choe, H., Parolin, C., Ruffing, N., Borsetti, A., Cardoso, A. A., Desjardin, E., Newman, W., Gerarad, C. & Sodorski, J. (1996) *Nature* 384, 179–183.
42. Trkola, A., Dragic, T., Arthos, J., Binley, J. M., Olson, W. C., Allaway, G. P., Cheng-Mayer, C., Robinson, J., Maddon, P. J. & More, J. P. (1996) *Nature* 384, 184–187.
43. Lapham, C. K., Ouyang, J., Chandrasekhar, B., Nguyen, N. Y., Dimitrov, D. S. & Golding, H. (1996) *Science*, 274, 602–605.
44. Rucker, J., Samson, M., Doranz, B. J., Libert, F., Berson, J. F., Smyth, R. J., Collman, R. G., Broder, C. C., Vassart, G., Doms, R. W. & Parmentier, M. (1996) *Cell* 87, 437–446.
45. Luz, Z., Berson, J. F., Chen, Y., Turner, J. D., Zhang, T., Sharron, M., Jenks, M. H., Wang, Z., Kim, J., Hoxie, J. A., Peiper, S. C. & Doms, R. W. (1997) *Proc. Natl. Acad. Sci. USA* 94, 6426–6431.
46. Alkhatib, G., Ahuja, S. S., Light, D., Mummidi, S., Berger, E. A. & Ahuja, S. K. (1997) *J. Biol. Chem.* 272, 19771–19776.
47. Alkhatib, G., Berger, E. A., Murphy, P. M. & Pease, J. E. (1997) *J. Biol. Chem.* 272, 20420–20426.
48. Doranz, B. J., Lu, Z. H., Rucker, J., Zhang, T. Y., Sharron, M., Cen, Y. H., Wang, Z. X., Guo, H. H., Du, J. G., Accavitti, M. A., Doms, R. W. & Peiper, S. C. (1997) *J. Virol.* 71, 6305–6314.
49. Alkhatib, G., Locati, M., Kennedy, P. E., Murphy, P. M. & Berger, E. A. (1997) *Virology*, 234, 340–348.

It will be apparent to those skilled in the art that various modifications and variations can be made in the disclosed process and product without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims. All references cited herein are hereby incorporated by reference in their entireties.

What is claimed is:

1. A method for screening a drug or other pharmacologically-active agent for its ability to block HIV-1 infection of a cell line coexpressing human leukotriene B4 receptor and CD4 on its cell surface, said method comprising:

(a) identifying a cell line that coexpresses leukotriene B4 receptor and CD4 on its cell surface;

(b) propagating the cell line in vitro;

(c) exposing the cell line to the drug or other pharmacologically-active agent;

(d) exposing the cell line to a primary virus isolate under conditions appropriate for interaction of the primary virus isolate with cell surface-expressed receptors;

(e) removing or diluting the virus to a predetermined detection threshold;

(f) incubating the virus exposed cells for a time sufficient for viral replication to occur;

(g) assaying for virus replication or viral gene expression, and (h) optionally comparing the results of the assay for cells exposed to the drug or other pharmacologically-active agent with results of the assay for cells not exposed to the drug or other pharmacologically-active agent.

2. The method of claim 1, wherein the assay technique comprises visual observation of the cells for viral-induced cytopathic effects.

3. The method of claim 1, wherein the assay technique comprises harvesting culture material, exposing susceptible animals or cell lines to the harvested culture material, and quantitating infectivity.

4. The method of claim 1, wherein the assay technique comprises measuring levels of antibody binding.

5. The method of claim 1, wherein the assay technique comprises hybridizing nucleic acid sequences.

6. The method of claim 1, wherein the assay technique comprises measuring levels of viral protein expression.

7. The method of claim 1, wherein the cell line is an NIH3T3 cell line.

8. A method of facilitating infection of HIV, said method comprising transforming a $CD4^+$ cell with an expression vector comprising a polynucleotide sequence encoding human leukotriene B4 receptor, culturing the transformed cell such that the human leukotriene B4 receptor is expressed on the surface of the cell, and infecting said cultured transformed cell with intact HIV, wherein expression of both the leukotriene B4 receptor and CD4 facilitates infection of the cell with HIV.

9. A method of facilitating infection of HIV, said method comprising transforming a $CD4^-$ cell with a) an expression vector comprising a polynucleotide sequence encoding human leukotriene B4 receptor, and b) an expression vector comprising a polynucleotide sequence encoding CD4, culturing the transformed cell such that the human leukotriene B4 receptor and the CD4 are expressed on the surface of the cell, and infecting said cultured transformed cell with intact HIV, wherein expression of both the leukotriene B4 receptor and CD4 facilitates infection of the cell with HIV.

* * * * *

UNITED STATES PATENT AND TRADEMARK OFFICE
CERTIFICATE OF CORRECTION

PATENT NO. : 6,333,163 B1  
DATED : December 25, 2001  
INVENTOR(S) : Christer Owman Page 1 of 1

It is certified that error appears in the above-identified patent and that said Letters Patent is hereby corrected as shown below:

<u>Column 18,</u>  
Line 54, "expression," should read -- expression; --.

Signed and Sealed this

Seventh Day of May, 2002

*Attest:*

*Attesting Officer*

JAMES E. ROGAN  
*Director of the United States Patent and Trademark Office*